US007056474B2

(12) United States Patent
Dumas et al.

(10) Patent No.: US 7,056,474 B2
(45) Date of Patent: Jun. 6, 2006

(54) HYDROCARBON SENSOR AND COLLECTOR

(75) Inventors: James T. Dumas, Clinton Township, MI (US); Philip J. Johnson, Ann Arbor, MI (US)

(73) Assignee: Visteon Global Technologies, Inc., Van Buren Township, MI (US)

( * ) Notice: Subject to any disclaimer, the term of this patent is extended or adjusted under 35 U.S.C. 154(b) by 633 days.

(21) Appl. No.: 10/039,390

(22) Filed: Oct. 29, 2001

(65) Prior Publication Data

US 2003/0082824 A1 May 1, 2003

(51) Int. Cl.
*G01N 27/00* (2006.01)
*G01N 21/00* (2006.01)
*G01N 31/00* (2006.01)
*G01N 33/00* (2006.01)
*G01N 7/00* (2006.01)

(52) U.S. Cl. .............................. 422/98; 422/83; 422/88; 422/93; 422/94; 422/95; 422/96; 422/97; 73/1.01; 73/1.02; 73/23.2; 73/23.31; 73/23.32; 436/149

(58) Field of Classification Search .................... 422/83, 422/88, 93, 94–95, 96, 97, 98; 73/1.01, 1.02, 73/23.2, 23.31, 23.32; 436/149
See application file for complete search history.

(56) References Cited

U.S. PATENT DOCUMENTS 3,368,326 A 2/1968 Helvert
3,982,100 A * 9/1976 Hervert ...................... 219/553
4,259,096 A 3/1981 Nakamura et al. ............ 55/316
4,261,717 A 4/1981 Belore et al.
4,280,360 A 7/1981 Kobayashi et al.
4,375,204 A 3/1983 Yamamoto
4,418,662 A 12/1983 Engler et al.
4,631,952 A 12/1986 Donaghey
5,088,466 A 2/1992 Tada .......................... 123/519
5,265,417 A * 11/1993 Visser et al. .................. 60/274
5,355,671 A * 10/1994 Maus et al. ................... 60/274
5,798,270 A * 8/1998 Adamczyk et al. ......... 436/143
5,875,768 A 3/1999 Schenk et al.
5,898,107 A 4/1999 Schenk
5,934,260 A 8/1999 Gadkaree et al. ........... 123/520
5,935,398 A * 8/1999 Taniguchi et al. .......... 204/424
6,000,217 A * 12/1999 Hochmuth ................... 60/274
6,097,011 A * 8/2000 Gadkaree et al. ........... 219/553
6,102,085 A 8/2000 Nanaji

FOREIGN PATENT DOCUMENTS

EP 1110593 A1 6/2001
JP 2001-33412 2/2001
JP 2001-234781 8/2001

OTHER PUBLICATIONS

Combined Search and Examination Report issued for British patent application No. 0221830.3 on Feb. 26, 2003, pp. 1–6.

* cited by examiner

*Primary Examiner*—Jill Warden
*Assistant Examiner*—Brian Sines
(74) *Attorney, Agent, or Firm*—Brinks Hofer Gilson & Lione

(57) ABSTRACT

A hydrocarbon sensor and collector. An element that is capable of absorbing and releasing hydrocarbons is positioned in the air intake system of a vehicle, upstream from the engine and wholly in the airflow. The element has a plurality of chambers defined in it that allow air to pass through the element. The hydrocarbon sensor and collector also includes a means for detecting the level of hydrocarbons absorbed by the element.

29 Claims, 3 Drawing Sheets

Fig. 1
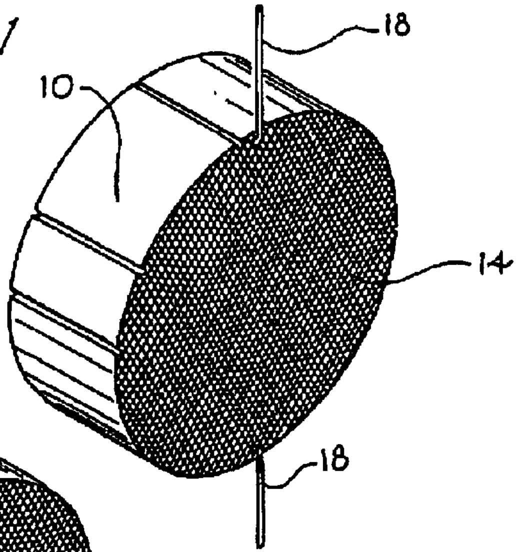
Fig. 2
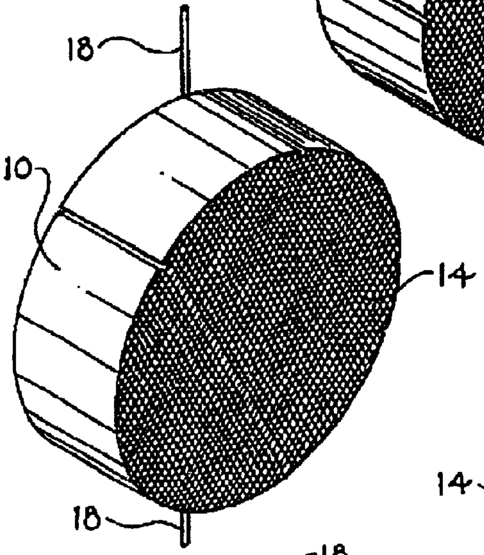
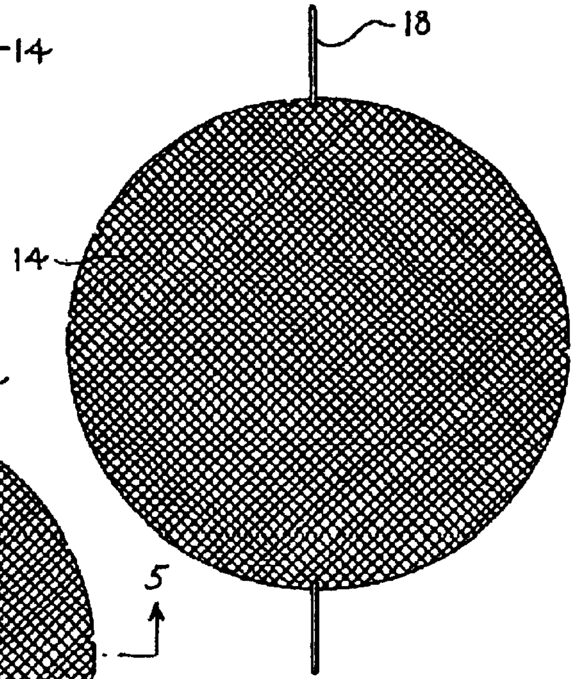
Fig. 3
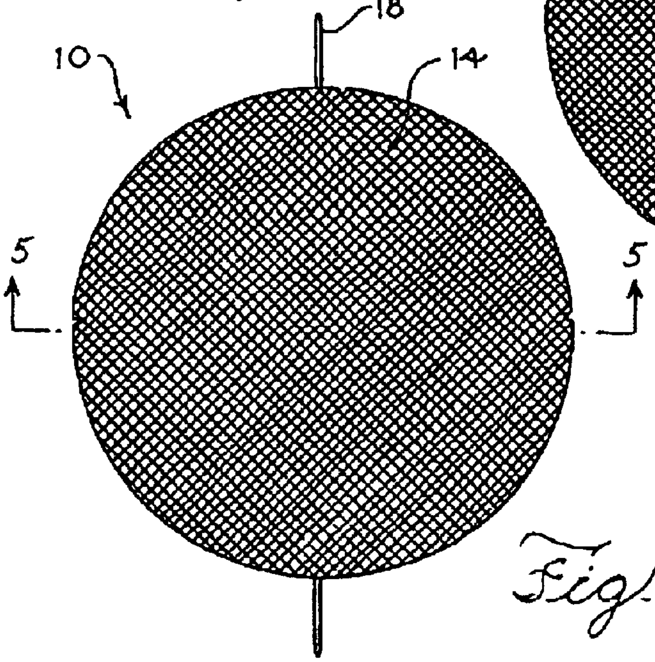
Fig. 4

HYDROCARBON SENSOR AND COLLECTOR

FIELD OF THE INVENTION

The invention relates generally to the field of engine air intake systems. Specifically, the invention relates to a hydrocarbon sensor and collector for use in an engine air intake system.

DESCRIPTION OF THE RELATED ART

Due to laws requiring the reduction of the levels of hydrocarbons that vehicles may emit into the atmosphere, it is necessary for automotive designers to include systems in vehicles to measure and control emissions. Hydrocarbons are released in a vehicle's exhaust, as well as from the engine, even when it is not operating. Hydrocarbons remaining from engine reactions can leak out of the engine through the engine's air intake.

The first step in reducing hydrocarbon emissions is to measure the level of hydrocarbons present in the engine system. Many methods have been utilized to measure the level of hydrocarbons in the exhaust. For example, U.S. Pat. No. 5,798,270 discloses a method for measuring the hydrocarbon level in vehicle exhaust gas by placing a hydrocarbon absorbing material in the exhaust stream of the vehicle. The hydrocarbon absorbing material is connected to a sensor. The sensor is connected to an on-board diagnostic system that monitors the exhaust emissions and notifies the operator when the hydrocarbon level exceeds a certain level. This method does not reduce the hydrocarbon emissions by any significant amount. U.S. Pat. Nos. 6,102,085 and 5,935,398 also disclose hydrocarbon-measuring systems. These systems evaluate the level of hydrocarbons present in the exhaust; they do not store or reduce the hydrocarbons emitted.

Apart from measuring the level of hydrocarbons in the exhaust, it is thus beneficial reduce the level of hydrocarbons. One method of doing so is to absorb hydrocarbons from the exhaust flow via a filter-like device. A problem arises, however, wherein the absorbing element eventually becomes saturated with hydrocarbons and is no longer able to function effectively. It would be beneficial to have a hydrocarbon-collecting element that would not have this limitation. Such an element could also be used to condition the air intake flow to increase engine capacity as well as for implementing a hydrocarbon-measuring feature.

BRIEF SUMMARY OF THE INVENTION

In one embodiment of the present invention, a hydrocarbon sensor and collector is provided. An element that is capable of absorbing and releasing hydrocarbons is positioned in the air intake system of a vehicle, upstream from the engine and wholly in the airflow. The element has a plurality of chambers defined in it that allow air to pass through the element. The hydrocarbon sensor and collector also includes a means for detecting the level of hydrocarbons absorbed by the element.

In a second embodiment of the present invention, a hydrocarbon sensor and collector is provided. An element capable of absorbing and releasing hydrocarbons has a plurality of chambers defined in it and is positioned in the air intake flow of an engine such that all the air entering the engine passes through the element. A circuit is in communication with the element and the circuit is capable of measuring the level of hydrocarbons absorbed by the element.

In a third embodiment of the present invention, a method for releasably absorbing hydrocarbons in an engine air intake is provided. The method comprises the steps of positioning a hydrocarbon absorbing element in the air intake system upstream from the engine and conductively connecting the element to a circuit capable of measuring the level of hydrocarbons in the air intake.

BRIEF DESCRIPTION OF SEVERAL VIEWS OF THE DRAWINGS

FIG. 1 is a perspective view of an embodiment of the hydrocarbon collecting and measuring element of the present invention showing chambers having a square shape;

FIG. 2 is a perspective view of the opposite side of the hydrocarbon collecting and measuring element of FIG. 1;

FIG. 3 is a top plan view of the hydrocarbon collecting and measuring element of FIG. 1;

FIG. 4 is a bottom plan view of the hydrocarbon collecting and measuring element of FIG. 1;

DETAILED DESCRIPTION OF THE PREFERRED EMBODIMENTS OF THE INVENTION

Figure 5:
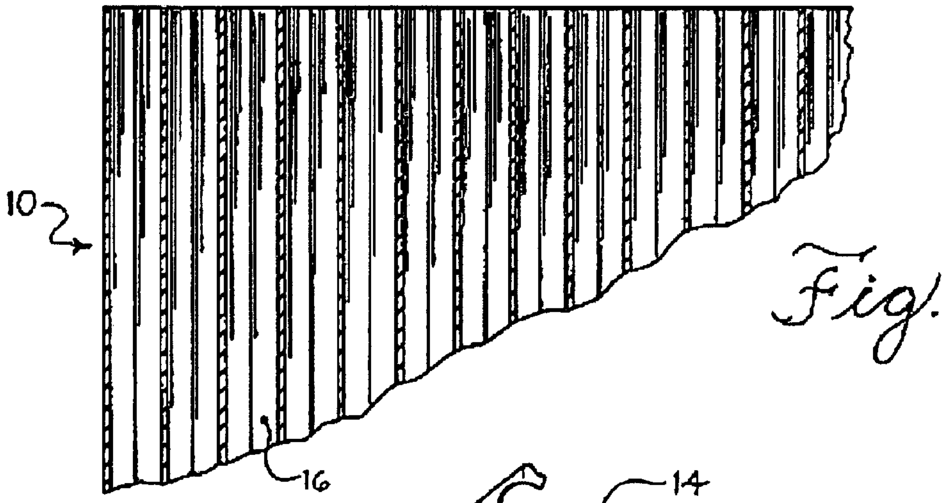
FIG. 5 is a close-up cross-sectional view along the line 5—5 of FIG. 4.

Referring in combination to FIGS. 1–5 and 8, a preferred embodiment of the present invention is shown. An element 10 is preferably constructed from a material that can absorb hydrocarbons. The element 10 could be constructed entirely from carbon, or could be constructed from carbon mixed with a binder material such as gray clay or ceramic. A preferred mixture comprises 10–30% binder material. The material is preferably able to release hydrocarbons that have been absorbed. This allows the element 10, when in place in a vehicle air intake, to absorb hydrocarbons when the engine is not operating and release these hydrocarbons when the engine is operating.

When the engine is not operating, hydrocarbons tend to leak out of the engine system and escape the vehicle thorough the air intake system. The element 10 is preferably positioned in the air intake tube 12 such that air must pass through the element 10 to escape the air intake tube 12 to the environment. The preferred position of the element 10 is upstream from the engine and wholly located in the airflow. When hydrocarbons are moving at a slow rate, such as when the engine is not pulling air into the air intake tube 12, the element 10 can absorb the hydrocarbons. An example of a preferred range of this rate is an evaporative flow of about 0.06–0.60 cc/minute. This prevents about 90–99% of the hydrocarbons from escaping. This percentage can be increased or decreased depending on the material used to construct the element 10. For example, the more carbon the element 10 contains the higher the absorbency. The total surface area of the element 10 and the thickness of the element 10 itself will also impact the absorbency.

The preferred embodiment of the element 10 is also self-regenerating. Rather than absorbing hydrocarbons and trapping them in the element 10 until the element 10 is saturated, the hydrocarbons may be relatively easily released from the element 10. The release occurs when the engine is operating and pulling air into the air intake tube 12 at a moderate to high rate. Preferably, when air passes though the element 10 at a moderate to high rate, the hydrocarbons trapped in the element 10 are pulled out and travel down the air intake tube 12 to the engine, where they are burned off. By allowing the hydrocarbons to be released from the element 10, the preferred embodiment of the invention is self-regenerating, and the element 10 does not have to be replaced over the lifetime of the vehicle as a result of hydrocarbon build-up.

The preferred embodiment of the element 10 also has a plurality of chambers 14 defined therein. The chambers 14 extend axially through the element 10, and have an opening on each side of the element 10. These chambers 14 facilitate the passage of air through the element 10. The chambers 14 also allow more of the surface of the element 10 to come into contact with hydrocarbon-laced air, therefore allowing the absorption of more hydrocarbons. The size and arrangement of the chambers 14 may be adjusted to allow for different amounts of flow through the element 10. Preferred measurements for the chambers 14 are in the range of 0.10–0.25 inches in radius or width if square-shaped chambers are utilized.

Figure 6:
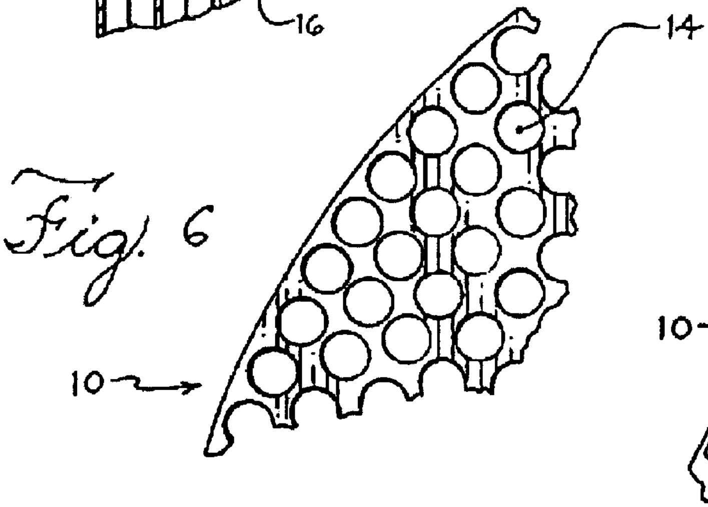
FIG. 6 is a close-up of an alternate embodiment of the hydrocarbon collecting and measuring element of the present invention showing chambers having a circular shape.
Figure 7:
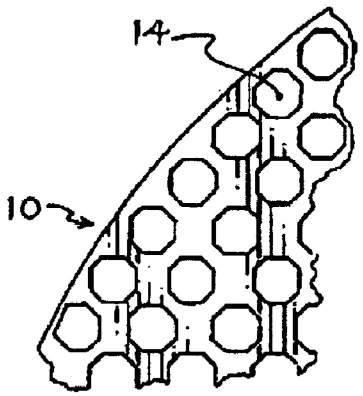
FIG. 7 is a close-up of an alternate embodiment of the hydrocarbon collecting and measuring element of the present invention showing chambers having an octagonal shape.
Figure 8:
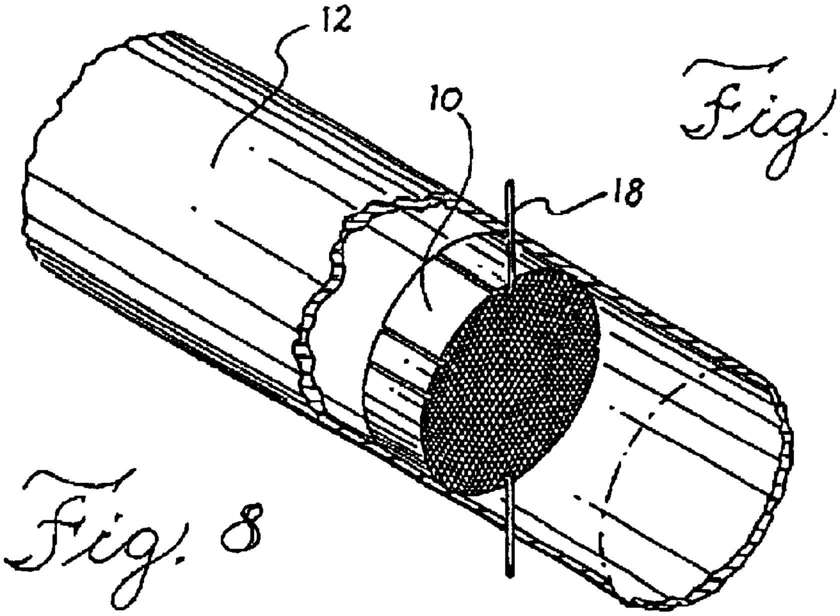
FIG. 8 is a perspective view of the hydrocarbon collecting and measuring element of FIG. 1 positioned in an air intake tube.

FIGS. 1–5 and 8 show a preferred embodiment of the element 10 of the present invention utilizing square-shaped chambers 14. In this embodiment, these chambers 14 preferably cover the entire surface of the element 10, creating numerous axial passages through the element 10. FIG. 5 shows a cross-sectional view of the axial passages 16 formed by the chambers 14 in the element 10. FIG. 6 shows an embodiment of the element 10 of the present invention utilizing circular chambers 14 and FIG. 7 shows an embodiment of the element 10 of the present invention utilizing octagonal chambers 14 arranged in a honeycomb pattern. These arrangements and shapes are examples, and it is noted that any number of different shapes and arrangements of the chambers 14 is possible and within the scope of the present invention.

In a further embodiment of the present invention, the chambers 14 in the preferred embodiment of the present invention allow the element 10 to function additionally as an airflow conditioner. By adjusting the shape, length, and arrangement of the chambers 14 in the element 10, a straighter, more efficient airflow is created. The plurality of small chambers 14 in the element 10 substantially prevents swirling conditions that are normally present in the air intake tube 12. By dividing the cross-sectional area into this multitude of smaller tubes in the form of chambers 14, the flow velocity is increased, resulting in a more efficient airflow profile. The chambers 14 help remove swirl and distortion of the airflow with a minimal overall pressure loss.

Figure 9:
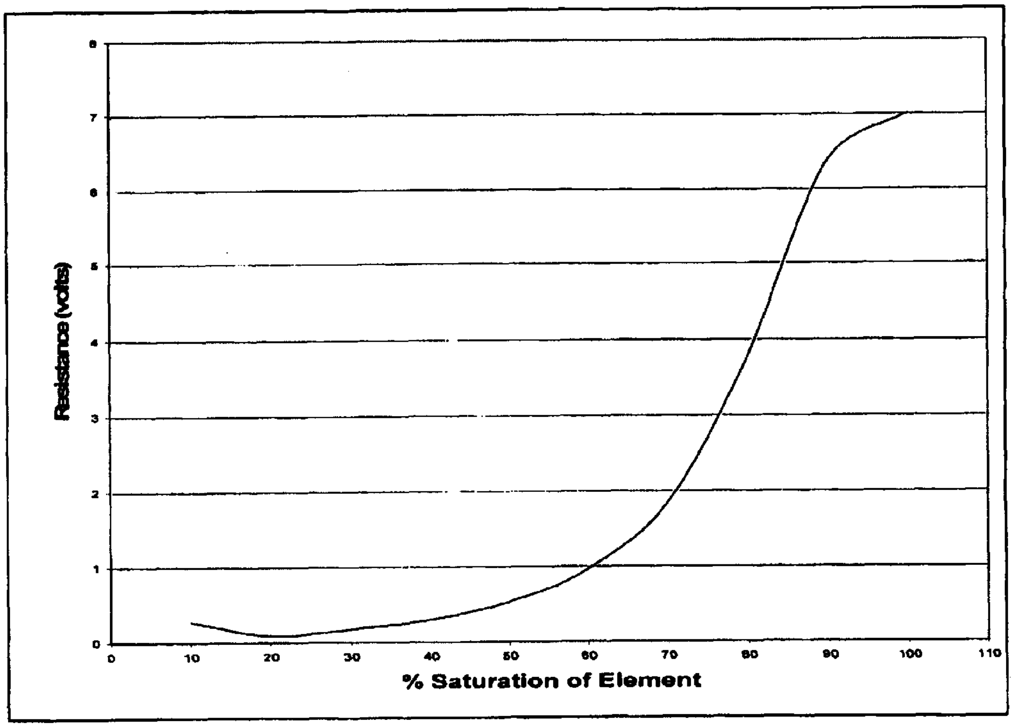
FIG. 9 is a table showing exemplary values of resistance, measured in volts, compared to the percentage of hydrocarbon saturation of the element.

The preferred embodiment of the present invention also includes a means for detecting the level of hydrocarbons in the airflow. Referring to FIGS. 1–4 and 8, the means for detecting the level of hydrocarbons in the air flow is shown as a plurality of wires 18 mounted to the element 10. These wires 18 are preferably molded to the element 10, but they could also be connected in any manner that allows the element 10 to conduct an electric charge, such as through the use of conductive epoxy. The wires 19 preferably extend through the air intake tube 12 and are preferably connected to a wheat stone bridge circuit (not shown). The circuit preferably includes a microprocessor (not shown) and is integrated into the on-board computer of the vehicle. The circuit is preferably set up such that the resistance of the element 10 can be measured by a diagnostic system, such as the on-board computer of the vehicle, or an outside system, such as a system used at a government emissions testing facility. As more hydrocarbons are trapped in the element 10, the electrical resistance of the element 10 will increase. This value can be measured and processed by the diagnostic system. Exemplary values of resistance measured in volts compared to the percentage of hydrocarbon saturation of the element 10 are shown FIG. 9.

Other means as known in the art may also be utilized to detect and measure the level of hydrocarbons in the element 10. Such alternative means include flame-ionized detectors, thermal conductivity detectors, acoustical propagation detectors, and optical detection means such as measuring the infra-red absorbency of the element 10.

The diagnostic system can provide feedback to the vehicle's on-board computer regarding the level of hydrocarbons present in the air intake tube 12. The information about the level of hydrocarbons could be used in any number of ways. For example, the hydrocarbon level could be used to adjust the fuel to air ratio or as a diagnostic tool to let an operator know if the system is leaking more fuel into the intake system than normal when the engine is not operating. This would be shown by excessive hydrocarbons being absorbed by the element 10 when the engine is not operating.

In another embodiment of the present invention, a method for releasably absorbing hydrocarbons in a vehicle air intake system and measuring the level of hydrocarbons in the system is provided. The steps of the method include first positioning an element 10 that is capable of both absorbing and releasing hydrocarbons in an air intake system, preferably in the air intake tube 12 and upstream from the engine. The element 10 is preferably formed from any of the materials described above and preferably includes a plurality of chambers 14 defined therein to provide axial passages for the air to pass through the element 10. The chambers 14 may be of any shape, and may be adjusted to condition the airflow in the air intake tube 12. The chambers 14 condition the airflow by straightening it out, creating a more efficient path of air through the air intake system. A designer can adjust the airflow by selecting a specific shape for the chambers 14. Examples of preferred chamber 14 shapes include circular, square, and octagonal as shown in FIGS. 1–7. The airflow may also be adjusted by selecting a specific width for the element 10 itself. The width of the element 10 as well as the shape of the chambers 14 also affects the hydrocarbon absorbency of the element 10. The more surface area of the element 10 that is exposed to the airflow, the greater the hydrocarbon absorbency.

The method also preferably includes the step of measuring the level of hydrocarbons absorbed by the element 10 by providing a plurality of wires 18 conductively connected to the element 10 and connecting the wires 18 to a circuit. The resistance of the element 10 increases as the element 10 absorbs hydrocarbons, and the circuit provides feedback to a diagnostic system which utilizes the change in resistance of the element to determine the level of hydrocarbons present in the element.

The element 10 of the preferred method preferably absorbs hydrocarbons at an evaporative airflow, such as when the engine is not operating. When the engine is not operating, air moves through the air intake tube 12 at a substantially slower rate than when the engine is operating. At this low rate, such as between 0.06–0.60 cc/min, hydrocarbons become trapped in the element 10. When the engine is operating, the moderate to higher rate of airflow pulls the trapped hydrocarbons out of the element 10 and into the engine, where they are safely burned off. This feature of the preferred method creates a self-regenerating element 10 that does not become saturated with hydrocarbons and thus does not normally have to be replaced.

It should be noted that there could be a wide range of changes made to the present invention without departing from its scope. As described, the thickness of the element 10 can be adjusted to change the amount of hydrocarbons absorbed. The shape and arrangement of the chambers 14 can also be adjusted to obtain the same results. The circular shape of the element 10 shown in the Figures is meant to be an example only and the shape of the entire element 10 can be made to match the shape of any air intake tube 12. The conductive connection of the element 10 to the circuit can also be accomplished through various other methods known in the art. The type of circuit to which the element 10 is conductively attached may also be replaced in any number of ways, such as with an analog input circuit or with other circuits known in the art that are capable of measuring the change in resistance of the element. Thus, it is intended that the foregoing detailed description be regarded as illustrative rather than limiting and that it be understood that it is the following claims, including all equivalents, which are intended to define the scope of the invention.

What is claimed is:

1. A hydrocarbon sensor for detecting hydrocarbons and a collector for collecting hydrocarbons in an air intake system of an engine, said sensor and collector comprising:

a purgeable hydrocarbon collecting element positioned in the air intake system upstream from said engine;

said purgeable hydrocarbon collecting element having a plurality of chambers defined therein, said chambers arranged so as to allow air to pass through said purgeable hydrocarbon collecting element; and a detecting means for detecting the level of hydrocarbons engaged with said purgeable hydrocarbon collecting element, the detecting means having a first portion connected to the purgeable hydrocarbon collecting element and a second portion connected to the purgeable hydrocarbon collecting element such that an electrical connection between the first portion and the second portion is completed by the purgeable hydrocarbon collecting element.

2. The hydrocarbon sensor and collector of claim 1, wherein said detecting means includes a plurality of wires connected to a diagnostic system.

3. The hydrocarbon sensor and collector of claim 2, wherein said wires are attached to said purgeable hydrocarbon collecting element with a conductive epoxy.

4. The hydrocarbon sensor and collector of claim 2, wherein said wires are molded to said purgeable hydrocarbon collecting element.

5. The hydrocarbon sensor and collector of claim 4, wherein said chambers are octagonal and arranged in a honeycomb pattern.

6. The hydrocarbon sensor and collector of claim 4, wherein said chambers are circular.

7. The hydrocarbon sensor and collector of claim 4, wherein said chambers are square.

8. The hydrocarbon sensor and collector of claim 1, wherein said purgeable hydrocarbon collecting element is configured to collect hydrocarbons in said chambers when said engine is not operating.

9. The hydrocarbon sensor and collector of claim 8, wherein said purgeable hydrocarbon collecting element is configured to release hydrocarbons when said engine is operating.

10. The hydrocarbon sensor and collector of claim 9, wherein said hydrocarbons are released as a result of an increased airflow present in said air intake system when said engine is operating.

11. The hydrocarbon sensor and collector of claim 10, wherein said purgeable hydrocarbon collecting element is formed from carbon mixed with a binder material.

12. The hydrocarbon sensor and collector of claim 11, wherein said binder material is gray clay.

13. The hydrocarbon sensor and collector of claim 11, wherein said binder material is ceramic.

14. The hydrocarbon sensor and collector of claim 10, wherein said purgeable hydrocarbon collecting element is formed from carbon.

15. The hydrocarbon sensor and collector of claim 1, wherein said wires are connected to a wheat stone bridge circuit.

16. A hydrocarbon sensor for detecting hydrocarbons and a collector for collecting hydrocarbons in an air intake system of an engine, said sensor and collector comprising:

a purgeable hydrocarbon collecting element having a plurality of chambers defined therein to allow air to pass through said purgeable hydrocarbon collecting element and said purgeable hydrocarbon collecting element positioned in an intake system of an engine such that substantially all of the airflow entering said engine passes through said purgeable hydrocarbon collecting element; and a circuit including an electrical connector and said purgeable hydrocarbon collecting element, said circuit being configured to detect the level of hydrocarbons engaged with said purgeable hydrocarbon collecting element.

17. The hydrocarbon sensor and collector of claim 16, wherein said purgeable hydrocarbon collecting element is a purgeable hydrocarbon collecting carbon element.

18. The hydrocarbon sensor and collector of claim 17, wherein said circuit includes a wheat stone bridge.

19. The hydrocarbon sensor and collector of claim 18, wherein said circuit includes a microprocessor.

20. The hydrocarbon sensor and collector of claim 19, wherein said circuit is integrated with the on-board computer of the vehicle.

21. The hydrocarbon sensor and collector of claim 20, wherein said purgeable hydrocarbon collecting carbon element is configured to collect hydrocarbons when an evaporative airflow passes through said purgeable hydrocarbon collecting carbon element.

22. The hydrocarbon sensor and collector of claim 21, wherein said purgeable hydrocarbon collecting carbon element is configured to release hydrocarbons when a moderate to high airflow passes through said carbon element.

23. A method for releasably collecting hydrocarbons and detecting the level of hydrocarbons in an air intake system of an engine, said method comprising the steps of:

positioning a hydrocarbon absorbing element having a plurality of chambers arranged so as to allow air to pass through said element in the air intake system upstream from the engine;

operatively connecting said element to a detecting means for detecting the level of hydrocarbons in said element; and detecting the level of hydrocarbons in said element.

24. The method of claim 23, further comprising the step of collecting hydrocarbons into said element when said engine is not operating.

25. The method of claim 24, further comprising the step of releasing said collected hydrocarbons when said engine is operating.

26. The method of claim 25, wherein the step of detecting the level of hydrocarbons in the element is performed by measuring the change in resistance of said element.

27. The method of claim 26, further comprising the step of defining chambers in said element.

28. The method of claim 27, wherein an airflow flows through said chambers and said chambers straighten said airflow as it flows through said element.

29. The method of claim 28, further including the step of adjusting the size and shape of said chambers and the thickness of said element.

* * * * *